(12) United States Patent
Demri et al.

(10) Patent No.: US 9,672,607 B2
(45) Date of Patent: Jun. 6, 2017

(54) IDENTIFICATION AND REGISTRATION OF MULTI-MARKER JIG

(71) Applicant: Biosense Webster (Israel) Ltd., Yokneam (IL)

(72) Inventors: Tamir Demri, Gilon (IL); Pinhas Abramovich, Tel Aviv (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 60 days.

(21) Appl. No.: 14/878,063

(22) Filed: Oct. 8, 2015

(65) Prior Publication Data

US 2017/0103505 A1  Apr. 13, 2017

(51) Int. Cl.
*G06K 9/00* (2006.01)
*G06T 5/50* (2006.01)
*G06T 7/00* (2017.01)
*G06F 19/00* (2011.01)
*A61B 6/00* (2006.01)
*A61B 90/00* (2016.01)

(52) U.S. Cl.
CPC ............... *G06T 5/50* (2013.01); *A61B 6/485* (2013.01); *A61B 6/503* (2013.01); *A61B 6/5235* (2013.01); *A61B 6/582* (2013.01); *A61B 90/39* (2016.02); *G06F 19/321* (2013.01); *G06T 7/0012* (2013.01); *G06T 7/0024* (2013.01); *A61B 2090/3966* (2016.02); *G06T 2200/04* (2013.01); *G06T 2207/10121* (2013.01); *G06T 2207/30048* (2013.01); *G06T 2207/30204* (2013.01)

(58) Field of Classification Search
USPC ........................................................ 382/132
See application file for complete search history.

(56) References Cited

U.S. PATENT DOCUMENTS

| | | | |
|---|---|---|---|
| 5,738,096 A | 4/1998 | Ben-Haim | |
| 6,044,132 A | 3/2000 | Navab | |
| 6,097,994 A | 8/2000 | Navab et al. | |
| 6,314,310 B1 | 11/2001 | Ben-Haim et al. | |
| 6,600,555 B2 | 7/2003 | McClenahan | |
| 8,300,941 B2 * | 10/2012 | Pilu ..................... | G06F 3/03545 178/18.01 |
| 2005/0259882 A1 | 11/2005 | Dewaele | |

(Continued)

OTHER PUBLICATIONS

European Search Report, Application No. 16192783.5, Dated Feb. 20, 2017.

*Primary Examiner* — Gregory F Cunningham
(74) *Attorney, Agent, or Firm* — Notaro, Michalos & Zaccaria P.C.

(57) ABSTRACT

Registering coordinate systems on an image is carried out by positioning a calibration jig having at least two collinear marker quadruples that are opaque to an imaging modality. Collinear quadruples are detected on an image of the jig and respective image cross ratios of the collinear quadruples are computed. Candidate lines are established by associating at least one collinear marker quadruple and at least one collinear image quadruple that have matching cross ratios. Respective registrations of the calibration jig with the image are performed using pairs of the candidate lines. One of the registrations is selected, wherein the selected registration has a residual that is smaller than a predetermined value.

22 Claims, 7 Drawing Sheets

(56) References Cited

U.S. PATENT DOCUMENTS

| | | | |
|---|---|---|---|
| 2007/0081695 A1* | 4/2007 | Foxlin | G06T 7/73 |
| | | | 382/103 |
| 2009/0034850 A1 | 2/2009 | Pilu | |
| 2009/0299174 A1* | 12/2009 | Wright | A61B 5/06 |
| | | | 600/424 |
| 2010/0046718 A1 | 2/2010 | Weiser | |
| 2014/0114173 A1* | 4/2014 | Bar-Tal | A61B 5/0035 |
| | | | 600/409 |

\* cited by examiner

IDENTIFICATION AND REGISTRATION OF MULTI-MARKER JIG

BACKGROUND OF THE INVENTION

1. Field of the Invention

This invention relates to image transformation by topological mapping. More particularly, this invention relates to combining a 2-dimensional medical image with a 3-dimensional map.

2. Description of the Related Art

Methods for 3-dimensional geometrical mapping and reconstruction of the endocardial surface are known in the art. For example, U.S. Pat. No. 5,738,096, whose disclosure is incorporated herein by reference, describes methods for mapping the endocardium based on bringing a probe into contact with multiple locations on a wall of the heart, and determining position coordinates of the probe at each of the locations. The position coordinates are combined to form a map of at least a portion of the heart.

Commercial electrophysiological and physical mapping systems based on detecting the position of a probe inside the body are presently available. Among them, the CARTO® 3 System, available from Biosense Webster, Inc., 3333 Diamond Canyon Road, Diamond Bar, Calif. 91765, is a system for automatic association and mapping of local electrical activity with catheter location.

In current cardiac catheterization systems, the operating physician must often observe two different images simultaneously, on two different screens: 2-dimensional fluoroscopic images of the thorax and 3-dimensional maps of the heart. Such 3-dimensional maps may be generated, for example, using magnetic tracking of the catheter tip in the heart. Both the fluoroscopic images and the 3-dimensional maps may show the catheter, but from different angles and perspectives. Because of the lack of automatic registration and coordination between the fluoroscopic and 3-dimensional views, the physician is required to switch his or her attention back and forth between the displays and mentally register the different information that they contain.

Some existing methods for registering anatomical images and electro-anatomical maps with 3-dimensional images acquired by a different modality generally rely on location data. The mapping catheter is placed at a number of known locations in the organ of interest, such as the heart, and the position coordinates are recorded. These same locations are marked or otherwise recorded in the 3-dimensional image. This technique generally requires the operator of the system to take time to find and mark the desired locations for the purpose of registration, in addition to the actions taken as part of the mapping procedure itself.

Various methods are known in the patent literature for automatically registering a fluoroscopic image with a 3-dimensional map. Such methods are described, for example, in commonly assigned U.S. Pat. No. 6,314,310 to Ben-Haim, et al., whose disclosure is incorporated herein by reference.

More recently, a different approach was disclosed in commonly assigned U.S. Patent Application Publication No. 2014/0114173, which is herein incorporated by reference. This document addresses placing a 2-dimensional fluoroscopic image of the thorax in registration with a 3-dimensional map functional electroanatomic map of the heart. A coordinate system registration module includes radiopaque elements arranged in a fixed predetermined pattern and configured, in response to the radiopaque elements generating a fluoroscopic image, to define a position of the module in a fluoroscopic coordinate system of reference. The module further includes one or more connections configured to fixedly connect the module to a magnetic field transmission pad at a predetermined location and orientation with respect to the pad, so as to characterize the position of the registration module in a magnetic coordinate system of reference defined by the magnetic field transmission pad.

One approach to image transformation is proposed in U.S. Pat. No. 8,300,941 to Pilu et al., which involves correcting for perspective distortion by identifying a best grid hypothesis for a surface coded pattern. The method comprises: extracting a set of straight line hypotheses from the coded surface pattern; clustering the straight line hypotheses by orientation; for each cluster, extracting a set of line pencil hypotheses; generating a set of regular grid hypotheses from pairs of the line pencil hypotheses; and determining the best regular grid hypothesis.

SUMMARY OF THE INVENTION

Embodiments of the invention provide a generic method for jig marker identification that is flexible to support jig orientation and position where not necessarily all the jig is visible in the image. Rather than using markers of different sizes, a constant size is employed.

There is provided according to embodiments of the invention a method for registering coordinate systems, which is carried out by positioning a calibration jig having markers that are opaque to an imaging modality in an imaged area. The markers comprise at least two collinear marker quadruples having respective cross ratios. The method is further carried out by producing with the imaging modality an image of the markers, detecting the markers on the image, identifying on the image collinear image quadruples of the detected markers, computing respective image cross ratios of the collinear image quadruples. The method is further carried out by defining candidate lines by associating at least one collinear marker quadruple and at least one collinear image quadruple that have matching marker cross ratios and image cross ratios according to predefined criteria, performing respective registrations of the calibration jig with the image using pairs of the candidate lines, determining residuals of the registrations, and selecting one of the registrations wherein the pair of the candidate lines thereof is associated with a qualifying residual that is smaller than a predetermined value.

According to another aspect of the method, at least a portion of the candidate lines have a plurality of collinear image quadruples.

According to a further aspect of the method, the markers lie along a single axis.

Yet another aspect of the method includes using the selected registration, reprojecting the markers onto the image, and thereafter establishing a new registration by locating others of the reprojected markers on the image.

According to a further aspect of the method, locating others of the reprojected markers includes determining a proximity between the reprojected markers and the detected markers.

According to one aspect of the method locating others of the reprojected markers includes scoring the reprojected markers according to a root mean square error of the reprojected markers and the detected markers.

According to another aspect of the method, establishing a new registration includes minimizing a residual error of reprojecting the markers in six degrees of freedom.

According to an additional aspect of the method, the markers are identical in size.

There is further provided according to embodiments of the invention a method for registering coordinate systems, which is carried out by positioning a calibration jig having radiopaque markers in an area irradiated by a fluoroscopic imager. The markers comprise at least two collinear marker quadruples having respective marker cross ratios. The method is further carried out by producing with the fluoroscope a fluoroscopic image of the markers, detecting the markers on the image, on the fluoroscopic image identifying collinear image quadruples of the detected markers, computing respective image cross ratios of the collinear image quadruples, defining candidate lines by associating at least one collinear marker quadruple and at least one collinear image quadruple that have matching marker cross ratios and image cross ratios according to predefined criteria, performing respective registrations of the calibration jig with the fluoroscopic image using pairs of the candidate lines, determining residuals of the registrations, and selecting one of the registrations wherein the pair of the candidate lines thereof is associated with a qualifying residual that is smaller than a predetermined value.

There is further provided according to embodiments of the invention an apparatus for registering coordinate systems, including a calibration jig having radiopaque markers, wherein the markers comprise at least two collinear marker quadruples having respective marker cross ratios. The apparatus further includes a processor, a memory accessible to the processor storing programs and data objects therein, wherein execution of the programs cause the processor to perform a method comprising detecting the markers on a fluoroscopic image, on the image identifying collinear image quadruples of the detected markers, computing respective image cross ratios of the collinear image quadruples, defining candidate lines by associating at least one collinear marker quadruple and at least one collinear image quadruple that have matching marker cross ratios and image cross ratios according to predefined criteria, performing respective registrations of the calibration jig with the image using pairs of the candidate lines, determining residuals of the registrations, and selecting one of the registrations wherein the pair of the candidate lines thereof is associated with a qualifying residual that is smaller than a predetermined value.

BRIEF DESCRIPTION OF THE SEVERAL VIEWS OF THE DRAWINGS

For a better understanding of the present invention, reference is made to the detailed description of the invention, by way of example, which is to be read in conjunction with the following drawings, wherein like elements are given like reference numerals, and wherein.

DETAILED DESCRIPTION OF THE INVENTION

In the following description, numerous specific details are set forth in order to provide a thorough understanding of the various principles of the present invention. It will be apparent to one skilled in the art, however, that not all these details are necessarily needed for practicing the present invention. In this instance, well-known circuits, control logic, and the details of computer program instructions for conventional algorithms and processes have not been shown in detail in order not to obscure the general concepts unnecessarily.

Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

In the description that follows, fluoroscopic images are described. This is by way of example and not of limitation. The processes describe herein are equally applicable to 2-dimensional images produced by many modalities, e.g., magnetic resonance images, computed tomography images, optical images and standard X-ray images.

Figure 1:
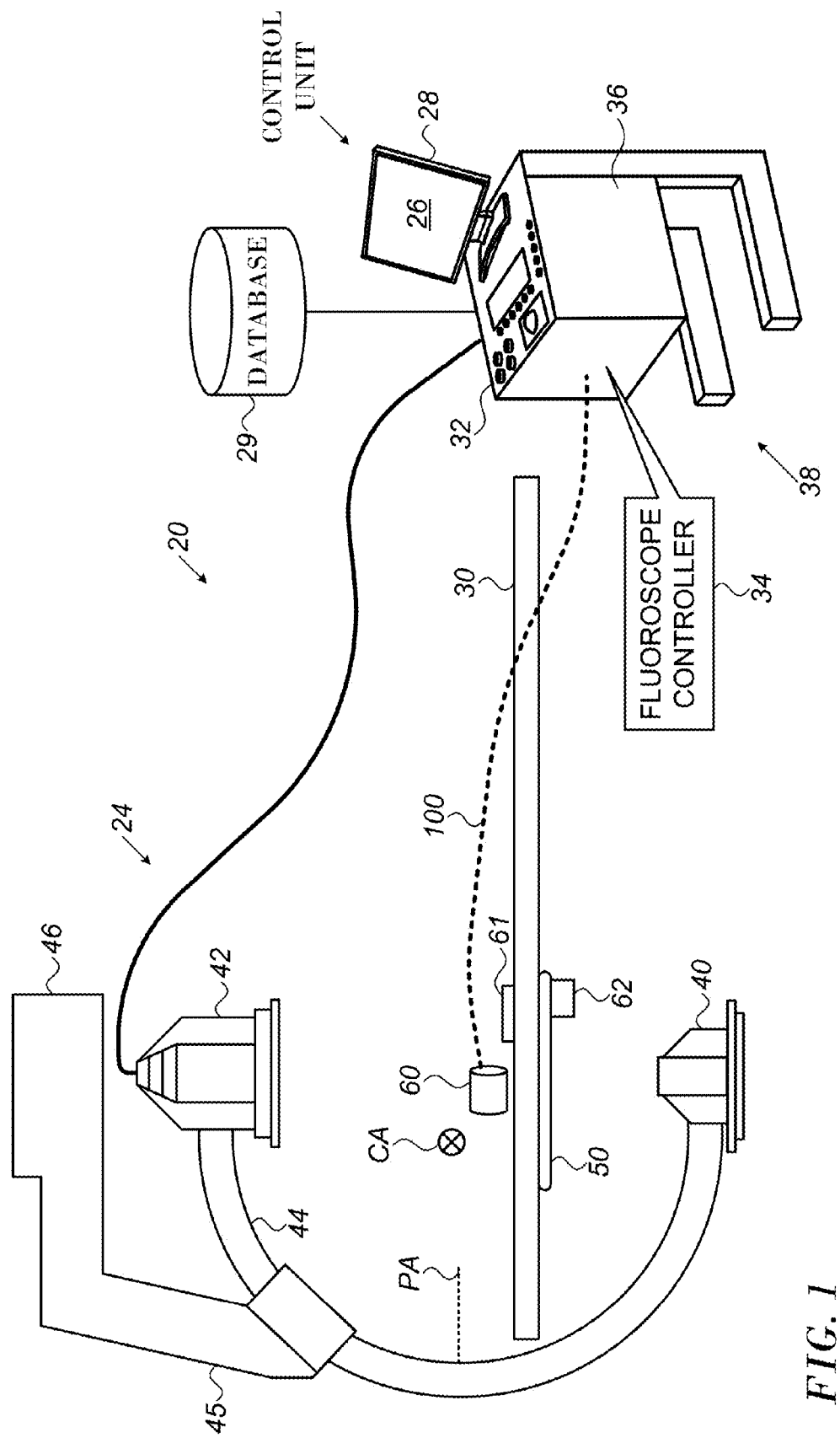
FIG. 1 is a schematic diagram illustrating a fluoroscopic image and magnetic mapping integration system in a calibration phase, according to an embodiment of the present invention.

Turning now to the drawings, reference is initially made to FIG. 1, which is a schematic diagram illustrating a fluoroscopic image and magnetic mapping integration system 20 in a calibration phase, according to an embodiment of the present invention. System 20 combines a 3-dimensional map of a body organ that is acquired by a magnetic tracking system 22, with a 2-dimensional fluoroscopic image of the patient acquired by a fluoroscope 24, so forming a combined display 26 that is presented to an operator of system 20 on a screen 28. In the calibration phase for system 20 illustrated in FIG. 1 the patient is not present. In a subsequent operational phase of system 20, illustrated in FIG. 5, the patient is assumed to be lying on a table 30 of system 20, and magnetic tracking system 22 and fluoroscope 24 acquire the 3-dimensional map and 2-dimensional image of the patient, as described in more detail below. Typically the 2-dimensional image acquired by the fluoroscope is of the chest of the patient, and the body organ mapped by the magnetic tracking system comprises the heart of the patient.

While in practice system 22 and fluoroscope 24 may typically be configured as separate physical units with separate control units, in the present description, for simplicity, system 20 is assumed to be operated by a single control unit 32.

Control unit 32 comprises a fluoroscope controller 34 operating the fluoroscope, and a magnetic system controller 36 operating the magnetic tracking system, and the unit is under overall control of a system processor 38, the processor, inter alia, generating combined display 26 on screen 28.

The processor 38 typically comprises a general purpose or embedded computer processor, which is programmed with suitable software for carrying out the functions described hereinbelow. Thus, although the processor 38 may sometimes be described as comprising a number of separate functional blocks, these blocks are not necessarily separate physical entities, but rather represent different computing tasks or data objects stored in a memory that is accessible to the processor. These tasks may be carried out in software running on a single processor, or on multiple processors. The software may be embodied on any of a variety of known nontransitory media for use with a computer system, such as a diskette, or hard drive, or CD-ROM. The code may be distributed on such media, or may be distributed to the processor 38 from the memory or storage of another computer system (not shown) over a network. Alternatively or additionally, the processor 38 may comprise a digital signal processor or hard-wired logic. The processor 38 typically includes memory storage for a database 29.

Fluoroscope 24 comprises an X-ray source 40 and a detector 42, the radiator and detector being mounted on opposite ends of a C-arm 44, assumed herein to comprise an arc of a circle. C-arm 44 is typically held at a lower end 45 of an L-arm 46, the L-arm being attached at its upper end to a ceiling of an operating theater, or at its lower end to the operating theater floor. C-arm 44 may be rotated around a horizontal pivot axis PA, which in the diagram is in the plane of the paper. C-arm 44 may also rotate around a C-arm axis CA, which is perpendicular to the plane of the paper and which passes through the center of the C-arm circle. Nominally, the two axes intersect at the C-arm center of rotation, also termed the iso-center, and are orthogonal to each other. The operator of system 20 is able to adjust rotations of fluoroscope 24 about axes PA and CA, as well as other geometrical parameters of the fluoroscope, using fluoroscope controller 34. (As described in more detail below, the calibration phase provides adjustments to nominal properties of fluoroscope 24, such as the ones exemplified above.)

In order to register coordinate systems, or frames of reference of fluoroscope 24, system 20 in its calibration phase, uses one or more registration elements. A given registration element has the property that its location and orientation may be determined simultaneously in both coordinate systems. Embodiments of the present invention use as a registration element a helix calibration jig 60. Helix calibration jig 60, also referred to herein as jig 60, is described in more detail with reference to FIG. 2.

Two coordinate systems, one based on location pad 50, and one based on registration module 62, are present in system 20.

Figure 2:
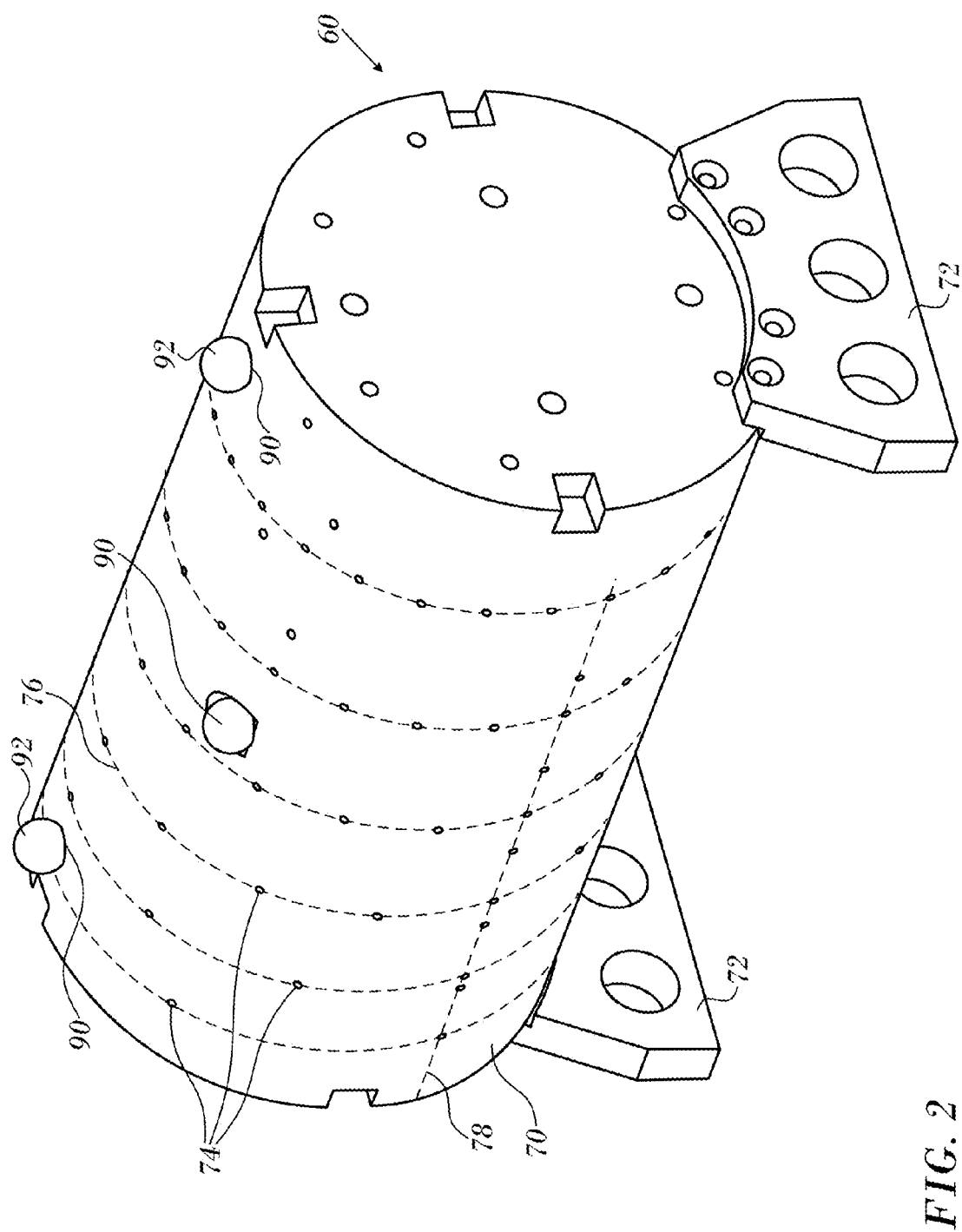
FIG. 2 is a schematic perspective diagram of a helix calibration jig used in the calibration phase, according to an embodiment of the present invention.

Reference is now made to FIG. 2, which is a schematic perspective diagram of the jig 60, according to an embodiment of the present invention. As will be apparent from the following description, jig 60 is "visible" in the fluoroscope system, to an extent that its position therein can be determined. Jig 60 is formed as a plastic cylinder 70, which may be placed, using attached supports 72, on table 30, so that the axis of the cylinder is parallel to the table. Cylinder 70 has identical metal spheres 74 embedded in the cylinder. Metal spheres 74 provide good contrast fluoroscopic images at detector 42. The spheres 74 may have any convenient size, so long as they are the identical in size. The use of identical spheres allows for flexibility of jig positioning, as constraints required by size considerations of the markers are avoided entirely. Spheres 74 are arranged in a helical pattern 76 within the cylinder, the helical pattern being configured to have a varying period length. In addition, within each period there are a different number of spheres. The helical pattern is illustrated by broken lines connecting spheres 74 of the helix. Moreover, there are at least two sets of collinear markers, each set comprising four markers, referred to as quadruples. The inter-marker distances in the jig 60 are known and may be encoded to enable unique identification.

In a disclosed embodiment of the present invention cylinder 70 has an approximate diameter of 120 mm, and an overall length of helical pattern 76 is approximately 200 mm. In the disclosed embodiment spheres 74 are arranged to define six periods, and Table 1 below gives exemplary lengths of each period in a direction parallel to an axis of cylinder 70, as well as exemplary numbers of spheres 74 within each period. Typically, spheres 74 are distributed evenly within each period.

TABLE 1

| Helix period length [mm] | Number of spheres 72 in the period |
|---|---|
| 20 | 7 |
| 25 | 11 |
| 30 | 15 |
| 35 | 19 |
| 40 | 23 |
| 45 | 27 |

Further spheres 74 may be added to those of helical pattern 76. For example, more spheres 74 have been added to form straight lines 78 of spheres, lines 78 corresponding to terminations of the helical periods.

The different lengths of the helical pattern periods, together with the different numbers of spheres 74 in each period, enable fluoroscope controller 34 to uniquely identify each of the spheres 74. Adding further spheres to the helical pattern, as described above, further facilitates fluoroscope controller 34 in identifying spheres 74. The identification of spheres 74 is used in registering 2-dimensional images with the fluoroscope, as described below.

In some embodiments cylinder 70 comprises retro-reflectors 90 wherein removable balls 92 may be positioned. Typically the retro-reflectors are arranged symmetrically in cylinder 70, in a plane parallel to table 30 and may be used, with the aid of a laser for tracking the position of jig 60 on table 30. In an alternative embodiment, other metal spheres, generally similar to spheres 74, may be added to jig 60 to further aid in its positioning.

Registration.

Figure 3:
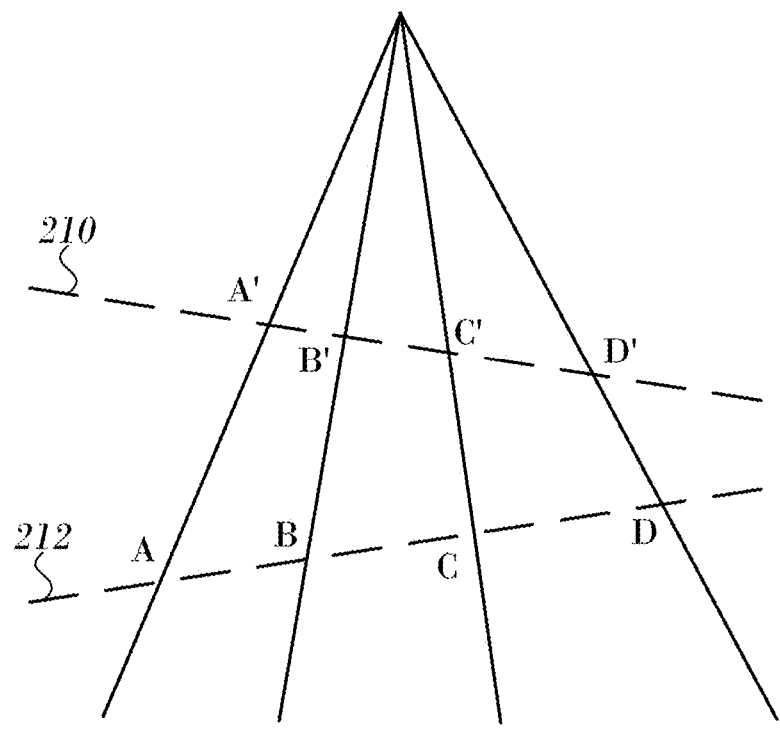
FIG. 3 is a diagram illustrating aspects of projective geometry, which are applied in accordance with an embodiment of the invention.

Reference is now made to FIG. 3, which is a diagram illustrating aspects of projective geometry, which are applied in accordance with an embodiment of the invention.

The method relies on two properties of projective geometry:

(1) A line 210 in space is projected to a line 212 in an image (2) If points A, B, C, D are a quadruple of collinear points in line 212, then the cross ratio is defined as (A, B; C, D)=(AC*BD)/(BC*AD). The cross ratio of a quadruple of collinear points is invariant under projection. In FIG. 3 the points A, B, C, D are projections of points A', B', C', D' in line 210, respectively. Thus, the cross ratios (A, B; C, D) and (A', B'; C', D') are equal.

Initial registration of the jig with a 2-dimensional image according to the principles of the invention requires a minimum of two lines, each having at least four collinear markers visible in the image. Reference is now made to FIG.

4, which is a flow chart of a method of jig registration with a 2-dimensional image in accordance with an embodiment of the invention. The process steps in this and other flow charts herein are shown in a particular linear sequence for clarity of presentation. However, it will be evident that many of them can be performed in parallel, asynchronously, or in different orders. Those skilled in the art will also appreciate that a process could alternatively be represented as a number of interrelated states or events, e.g., in a state diagram. Moreover, not all illustrated process steps may be required to implement the method.

At initial step 214 a relationship is determined between fluoroscopic geometrical parameters and the fluoroscopic projection function. This can be done using a calibrated model if available. Alternatively, a nominal, non-calibrated fluoroscopic model can be used. The model provides a sufficient approximation to enable further refinement in the steps described below.

Figure 5:
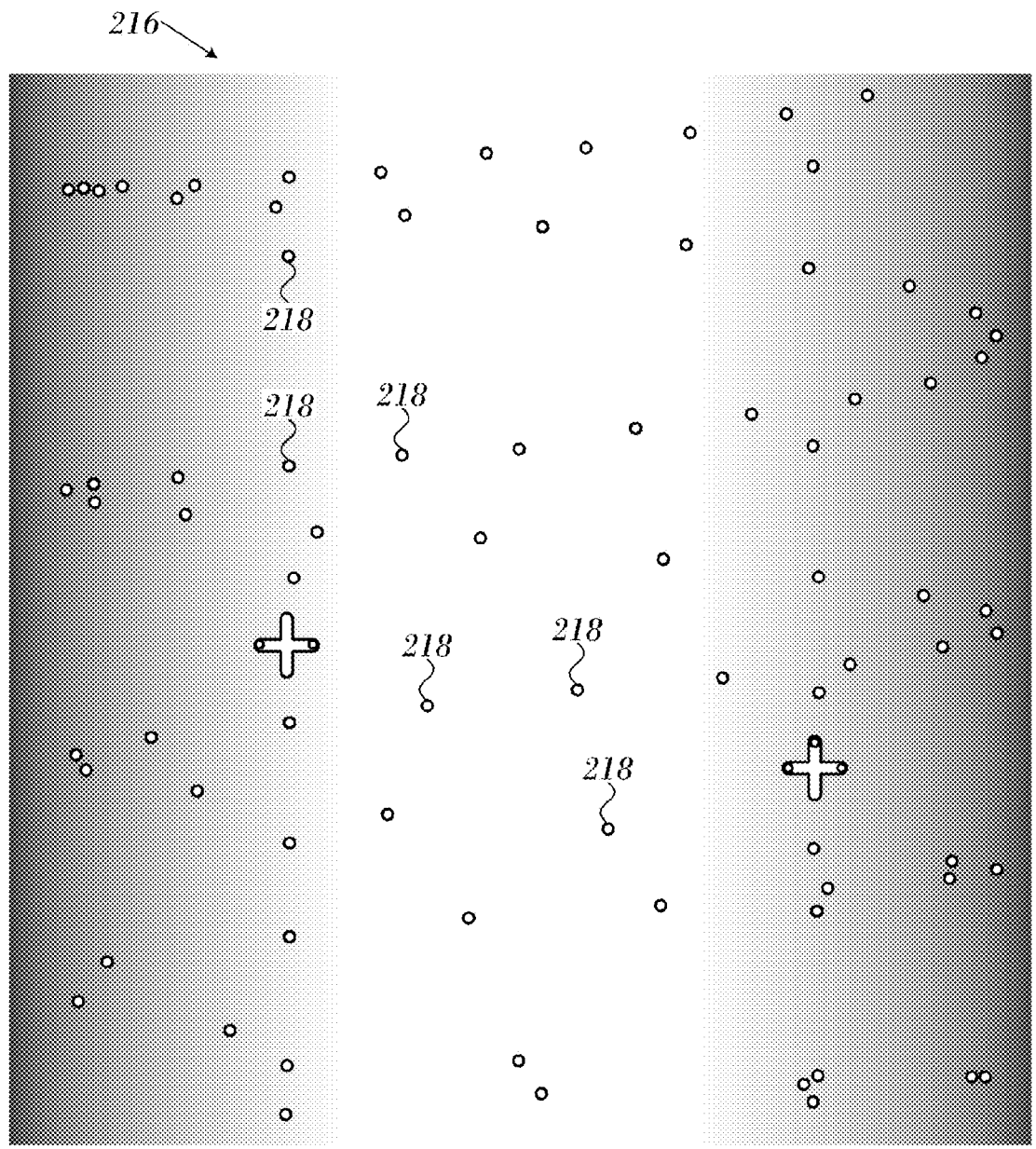
FIG. 5 is an exemplary projection of a jig onto a 2-dimensional image in accordance with an embodiment of the invention.

Reference is now made to FIG. 5, which is an exemplary projection 216 of jig 60 (FIG. 2) onto a 2-dimensional image, in accordance with an embodiment of the invention. Markers 218 are projections of the spheres 74 on the jig 60.

Figure 4:
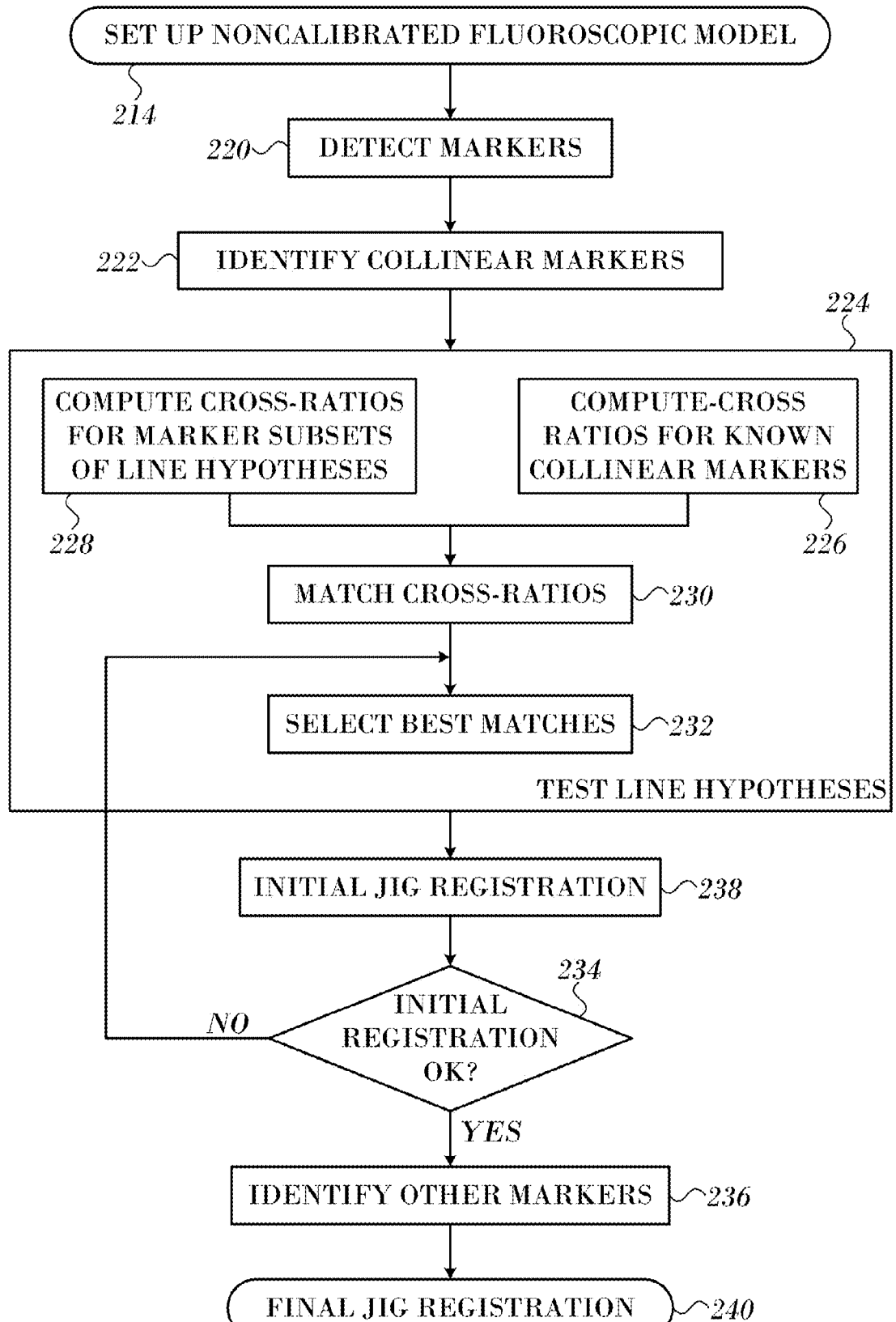
FIG. 4 is a flow chart of a method of jig registration with a 2-dimensional image in accordance with an embodiment of the invention.

Reverting to FIG. 4, at step 220 the markers 218 (FIG. 5) are detected on the projection 216. This step may be performed methods such as template matching, ellipse detection or edge detection. These are conventional image processing techniques and are not further discussed herein. Step 220 results in a set of detected markers.

Next, at step 222 collinear markers are identified on the projection 216 in the set of markers that was generated in step 220. This step may be performed by line fitting using known methods such as random sample consensus (RANSAC) or the Hough transform. Step 222 produces a set of line hypotheses, i.e., subsets comprising at least quadruples of markers that are candidates for collinearity. Each quadruple defines a cross ratio. The list of all quadruples that are candidates for collinearity defines a signature. The subsets include all possibilities where one or more markers are missing, and the list specifies the missing markers. For example in a line of 5 markers there is one 5-marker subset and five 4-marker subsets. Each subset is stored specifying the respective indices of the members of that subset Next, at step 224 the line hypotheses developed in step 222 are evaluated by matching their cross ratios against the cross ratios of the known inter-marker distances on the jig within each line. Step 224 comprises several procedures:

In step 226 all known subsets of four or more collinear markers in the jig are evaluated in order is to cover cases of undetected markers or markers out of image. Each quadruple defines a cross ratio. Subsets of markers are created as to simulate all possible options where one or more markers are missing. The missing markers can be in various locations, and may even be outside the field of view shown in FIG. 6. For each subset we there is a "signature" that accounts for all possible cases. The signature can be determined using an efficiently implemented brute-force method, For all subsets of such markers cross ratios are computed by iterating over all quadruples within each subset, thereby creating subset-specific signatures. The cross ratio signatures are saved in a reference database 29 (FIG. 1). For example, cross ratios of all sets of four consecutive markers can be saved. Step 226 need be performed only once for each jig design. The results may be applied to all subsequently manufactured jigs having the same design.

In step 228 for each line hypothesis cross ratios are computed for each quadruple in each subset of markers on the image that pertain to that line hypothesis and were identified in step 222. Each quadruple defines a cross ratio. Subsets of markers are created as to simulate all possible options where any of the co-linear markers might be a false inlier, i.e., cases where there is a marker that accidently lies on a line on image but it is not co-linear on the jig mechanical structure. The line hypothesis cross ratios are signatures that are saved in an image cross ratio database in the same format as in the reference database obtained in step 226. Both the reference database and the image cross ratio database can be included in the database 29 (FIG. 1).

In a matching step 230 a search is conducted for matches between the cross ratio signatures obtained in step 228 and those obtained in step 226. The intent is to find potential matches between collinear markers in the image and their corresponding markers in the jig. Each match is an option for identification of the markers in the subset of markers. Matching is performed by comparing subsets of equal size. The cross ratios in step 228 and step 226 are compared by Euclidean distance to find correspondence of two sets of numbers. Alternatively other measurements of distance may be used. In any case a match is declared when a subset in the image and a subset in the jig are found to be closer to each other than a predefined threshold distance.

In step 232 the matches obtained in step 230 are prioritized according to the number of markers or alternatively, according to the root-mean-square error (RMSE) of the signature match, creating a prioritized list of line hypotheses matched to the two jig lines.

In step 238 an initial jig registration procedure is performed. An exhaustive pairwise selection of candidate lines from the line hypotheses chosen in step 232 is evaluated. The line pairs are evaluated in an order according to relevance and likelihood, Precedence is given to matches of larger subset. The first pair that to be evaluated is the largest subset in the image that matched to one line in the jig and the largest subset in the image that matched to the other line. If this does not produce a satisfactory initial registration, then progressively smaller subsets are tested. Each test requires initial registration and approval or rejection according to the minimum RMSE value. Other considerations include the location of markers in the image. Depending on the C-arm orientation, one line may be expected to be to the left (or right) of the second line. The quality of the cross ratio match quality may be another decisional criterion.

Step 238 yields one or more image line candidates to each of the jig lines (only one is a true match). Each pair of image line candidates matching to the two jig lines is then considered and evaluated in the following steps until reaching a valid registration. For efficiency, there is precedence to candidates having longer signatures (i.e., longer subsets). The first pair to be evaluated is the largest subset in image that matched to one line in the jig and the largest subset in image that matched to the other line. Additionally location of markers in image is another consideration.

Termination criteria for the evaluation algorithm are desirable, e.g., a threshold number of iterations. However, in practice a correct match is almost always reached within a few iterations. Jig registration with the image is performed using each such pair and residuals are determined by reprojecting the markers onto the image and measuring the distance between the detected markers on the first projection and on the reprojection.

Next, at decision step 234, it is determined if the initial jig registration is a qualifying residual, i.e., a residual that is smaller than a user-configured criterion. If the determination at decision step 234 is negative, then control returns to step 232 where another line pair is evaluated.

If the determination at decision step 234 is affirmative then control proceeds to step 236. Once a valid initial registration is determined, then at step 236 the rest of the detected markers are identified, based on the initial registration. This is accomplished by reprojecting the jig onto the image using the initial registration of the line pairs in step 238. Proximity criteria, i.e., the distance between the detected and reprojected markers, e.g., the RMSE, are used to identify the remaining markers. If the initial registration is adequate, then all the remaining markers will be located with minimal error.

Figure 6:
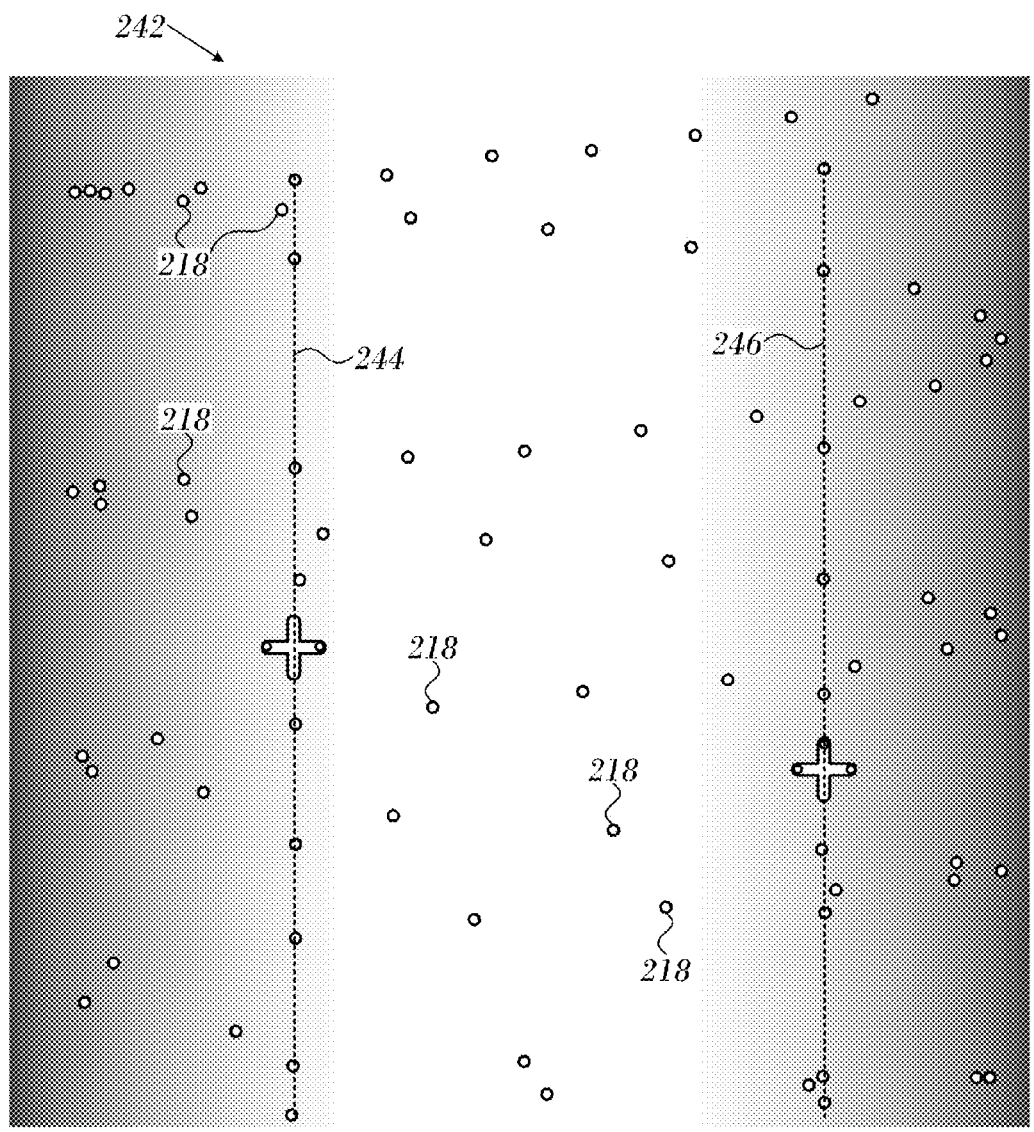
FIG. 6 is an exemplary projection of a jig onto a 2-dimensional image in accordance with an embodiment of the invention.

At final step 240 a final jig registration is performed using all the markers that were identified in step 236. This is done by a minimization function that finds the jig location and orientation in six degrees of freedom that yields the minimal residual error of the reprojection of the markers (identified in step 236). Reference is now made to FIG. 6, which is a fully registered projection 242 of jig 60 (FIG. 2) onto a 2-dimensional image, in accordance with an embodiment of the invention. Markers 218 are now uniquely identified by indicia, e.g., adjacent numerals. Lines 244, 246 were the best pair in the set of candidate lines used that were chosen in the successful initial registration and the subsequent full registration performed in steps 238, 240 (FIG. 4).

Alternate Embodiment

This embodiment is similar to the previous embodiment. However, step 238 (FIG. 4) is modified to perform initial jig registration in five degrees of freedom instead of six. This is done using a single chosen line hypothesis instead of two lines. This option is useful for jigs that are symmetric about a single axis, such as a rod having markers on the axis of symmetry. This embodiment conserves time and computer resources where it is only necessary to determine the axis of the chosen line in the image.

Figure 7:
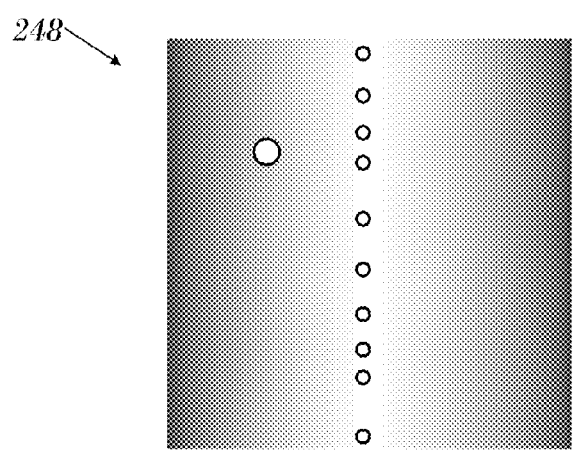
FIG. 7 is a projection of a jig having a single line of markers onto a 2-dimensional image, in accordance with an alternate embodiment of the invention.

Reference is now made to FIG. 7, which is a fully registered projection 248 of a jig having a single line of markers onto a 2-dimensional image, in accordance with an alternate embodiment of the invention. The distances between the markers are intentionally varied in order to enable a variety of cross ratios.

Figure 8:
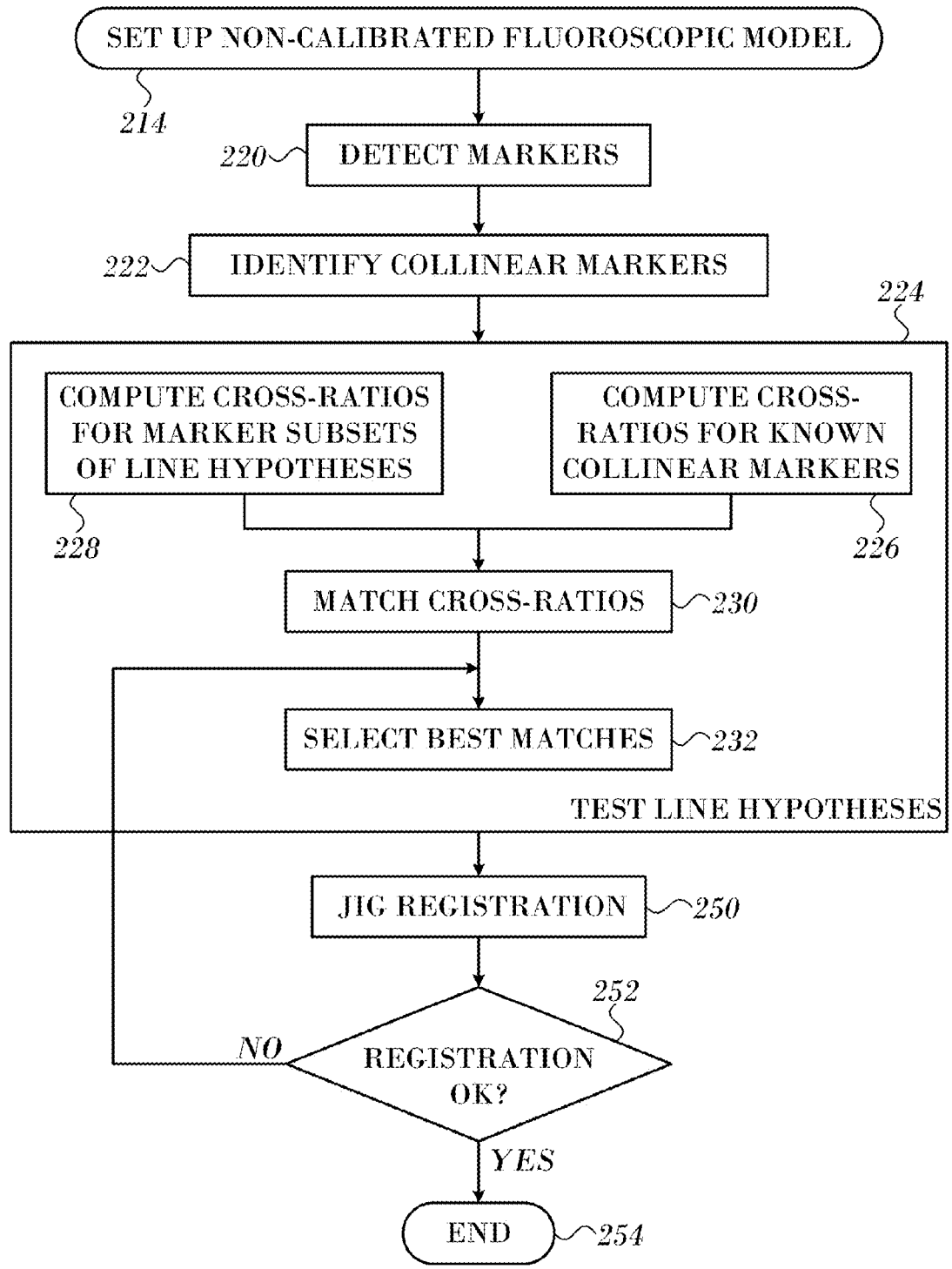
FIG. 8 is a flow chart of a method of jig registration with a 2-dimensional image in accordance with an alternate embodiment of the invention.

Reference is now made to FIG. 8, which is a flow chart of a method of jig registration with a 2-dimensional image in accordance with an alternate embodiment of the invention. The steps in FIG. 8 are identical to those described in the discussion of FIG. 4 until step 250. The details are not repeated in the interest of brevity.

In step 250 a complete jig registration is performed, rather than a tentative registration as described in the first embodiment.

Next, at decision step 252, it is determined if the registration performed in step 250 is acceptable. If the determination is negative, then control returns to step 232.

If the determination at decision step 252 is affirmative, then control proceeds to final step 254, where the procedure ends. Identification of other markers and a second registration as described in step 236 and final step 240 (FIG. 4) are unnecessary. Since the registration of step 250 resolves only five degrees of freedom, rotation of the linear jig about its own axis does not affect the projection.

Example

In this Example a laser tracking device was used to verify accuracy and repeatability of the above-described algorithms for calibration and registration of a helix jig. Calibration and registration results for different helix jig positions relative to a fluoroscopy system were compared. It was verified that the calculated transformation between the fluoroscopy system coordinate system and the laser tracker coordinate system remains constant.

Various calibration sequence and registration images were taken of the helix jig at different helix jig positions and orientations. Each helix jig position was also measured using the laser tracker.

From the helix jig position measurement obtained with the laser tracker, and the known mechanical position of retro-reflectors used for this measurement in the helix jig coordinate system, it is possible to calculate a transformation from the laser tracker coordinate system to the helix jig coordinate system. A Laser2Helix transformation was calculated for each helix jig position.

The result of each calibration and registration algorithm includes a calculated transformation from the helix coordinate system to the fluoroscope coordinate system. A Helix2Fluoro transformation was calculated for each calibration result and for each registration image.

From the above transformations, a transformation from the Fluoroscope coordinate system to the Laser Tracker coordinate system may be calculated as following:

$$\text{Fluoro2Laser}=(\text{Laser2Helix})^{-1}*(\text{Helix2Fluoro})^{-1} \quad \text{Eq.1:}$$

Thus, a Fluoro2Laser transformation was calculated for each calibration result and for each registration image. This transformation should be the same, independent of the helix jig position or calibration/registration images, since the fluoroscope coordinate system and the laser tracker coordinate system were constant throughout this test.

From the reference Helix2Fluoro transformation for each Helix Jig position, a reference Fluoro2Laser was calculated using Eq.1 above.

The above calculated transformations were utilized for the following comparisons to verify accuracy and repeatability of the fluoroscopy calibration tool that performs the calibration and registration algorithms.

Calibration Algorithm

Comparison between all Fluoro2Laser transformations calculated for the different calibration results.

Comparison between the projections of the same points in the fluoroscope coordinate system into the same images, taken at various C-arm positions, using the different calibration results.

Registration Algorithm

Comparison between all Fluoro2Laser transformations calculated for the different registration images taken for the same Helix Jig position.

Comparison between all Fluoro2Laser transformations calculated for all registration images taken with the C-arm at various positions, across all Helix Jig positions.

Note: Ideally, the above comparisons should yield values close to zero; the actual values are a measure of the algorithm repeatability.

Test Tools and Auxiliary Equipment.

Fluoroscopy system.

CARTO system with UNIVU module.

Laser Tracker (available from Faro Technologies, Inc, 250 Technology Park Lake Mary, Fla. 32746, USA) and retro-reflectors.

Helix Jig.

Matlab® software.

Analysis code, taken from Microsoft Visual Studio® Source Control).

FCT Fluoro Integration Algorithms, taken from Microsoft Visual Studio Source Control).

Test Procedure.

Calibration Algorithm Test Plan.

The helix jig was placed on the patient table in the fluoroscope COR and a calibration image sequence was collected, i.e., images were acquired at the following fluoroscope C-arm positions: LAO90; LAO60; LAO30; AP; RAO30; RAO60; RAO90; CRA20; CRA40; CAU20; and CAU40.

Data collection was repeated for several slightly different Helix Jig positions on the patient table, as detailed in Table 2 in the Results section below.

Data analysis was performed using the analysis code specified in the Tools and Equipment section, according to the method described in the Test Concept and Method section.

Registration Algorithm Test Plan.

The helix jig was placed on the patient table in the Fluoroscope COR and registration images were taken at various C-arm angles.

Data collection was repeated for several different patient table/helix jig positions on the patient table, as detailed in Table 6 in the Results section below.

Data analysis was performed using the analysis code specified in the Tools and Equipment section above, according to the method described in the Test Concept and Method section above.

Acceptance Criteria.

Calibration Algorithm:

Comparison between all Fluoro2Laser transformations calculated for the different calibration results shall yield a mean value that does not exceed 1 mm.

Comparison between the projections of the same points in the fluoroscope coordinate system into the same images, taken at various C-arm positions, using the different calibration results, shall yield a mean value that does not exceed 1 mm.

Registration Algorithm.

Comparison between all Fluoro2Laser transformations calculated for the different registration images taken for the same helix jig position shall yield a mean value that does not exceed 1 mm.

Comparison between all Fluoro2Laser transformations calculated for the different registration images taken with the C-arm at an AP position, across all helix jig positions, shall yield a mean value that does not exceed 1 mm.

Comparison between all Fluoro2Laser transformations calculated for the different registration images taken with the C-arm at an LAO90 position, across all Helix Jig positions, shall yield a mean value that does not exceed 1 mm.

Comparison between the reference Fluoro2Laser transformations calculated for the registration images for the different Helix Jig positions shall yield a mean value that does not exceed 1 mm.

Calibration Algorithm Test Results.

Table 2 below details the differences in helix jig position for the different calibration sequence images collected.

TABLE 2

Calibration data collection.

| Calibration folder name | Helix Jig position |
|---|---|
| T124248 | COR, Helix Jig placed at an angle relative to the y-axis |
| T135346 | COR, Helix Jig placed in parallel relative to the y-axis |
| T141140 | Helix Jig moved ~2 cm in y-axis |
| T142241 | Helix Jig moved ~2 cm in x-axis |
| T143508 | Helix Jig moved ~2 cm in y-axis & ~2 cm in x-axis (i.e., diagonally) |

The patient table position for all calibrations was [−54, −865, 930], except for the first calibration (T124248), where it was [−59, −864, 930]. The fluoroscope zoom setting for all calibrations was 42 cm.

Table 3 below shows the calibrated parameter values for the different calibrations.

TABLE 3

Calibrated parameters values for calibrations performed.

| Calibrated Parameters | T124248 | T135346 | T141140 | T142241 | T143508 |
|---|---|---|---|---|---|
| yAxisOffset (mm) | −1.74 | −1.25 | −1.08 | −1.61 | −1.51 |
| xyAxesAngle ( ) | 89.92 | 89.96 | 90.00 | 89.97 | 89.95 |
| radiusVectorCorToSourceX (mm) | 1.32 | 1.59 | 1.95 | 1.49 | 1.93 |
| radiusVectorCorToSourceY (mm) | −6.57 | −7.37 | −6.87 | −6.53 | −6.69 |
| radiusVectorCorToSourceZ (mm) | −748.6 | −748.9 | −749.1 | −748.6 | −749.3 |
| radiusVectorSourceToDetectorRotationAnglesX ( ) | 0.15 | 0.16 | 0.16 | 0.16 | 0.16 |
| radiusVectorSourceToDetectorRotationAnglesY ( ) | 0.02 | 0.06 | 0.07 | 0.05 | 0.06 |
| detectorRotationAnglesX ( ) | −0.20 | −0.38 | −0.30 | −0.28 | −0.25 |
| detectorRotationAnglesY ( ) | 0.098 | 0.039 | 0.013 | −0.224 | 0.198 |
| detectorRotationAnglesZ ( ) | −1.11 | −1.21 | −1.25 | −1.21 | −1.19 |
| detectorCenterOfRotationOffsetX (mm) | 0 | 0 | 0 | 0 | 0 |
| detectorCenterOfRotationOffsetY (mm Fixed) | 0 | 0 | 0 | 0 | 0 |
| pivotDeformationPolynomialParameters1 | −0.0068 | −0.042 | −0.043 | −0.070 | −0.023 |

TABLE 3-continued

Calibrated parameters values for calibrations performed.

| Calibrated Parameters | T124248 | T135346 | T141140 | T142241 | T143508 |
|---|---|---|---|---|---|
| pivotDeformationPolynomialParameters2 | −0.059 | −0.062 | −0.078 | −0.062 | −0.044 |
| pivotDeformationPolynomialParameters3 | −0.01814 | 0.0043 | 0.00031 | 0.0272 | −0.0163 |
| tubeDeformationYAxisPolynomialParameters1 | −0.0002 | 0.00013 | 0.00045 | −0.00012 | −0.00011 |
| tubeDeformationYAxisPolynomialParameters2 | −3.8E−05 | −0.00028 | −0.00025 | −0.00022 | −0.00026 |
| tubeDeformationXAxisPolynomialParameters1 | 0 Fixed | 0 Fixed | 0 Fixed | 0 Fixed | 0 Fixed |
| tubeDeformationXAxisPolynomialParameters2 | 0 Fixed | 0 Fixed | 0 Fixed | 0 Fixed | 0 Fixed |
| sidCorrectionCoef01 (mm Fixed) | −2.26 | −1.07 | −0.77 | −1.76 | −0.71 |
| primaryAngleCorrectionCoef01 | −0.00022 | −0.00027 | −0.00103 | −0.00032 | −0.0004 |
| secondaryAngleCorrectionCoef01 | 0.00021 | 0.00267 | 0.00339 | 0.00149 | 0.00150 |
| calibrationJigAxisAngle1 | −1.34 | −1.24 | −1.25 | −1.24 | −1.24 |
| calibrationJigAxisAngle2 | 1.13 | 1.19 | 1.19 | 1.19 | 1.19 |
| calibrationJigAxisAngle3 | 1.33 | 1.24 | 1.24 | 1.24 | 1.24 |
| calibrationJigTranslationX (mm) | 5.84 | 2.63 | 3.48 | −15.6 | 21.8 |
| calibrationJigTranslationY (mm) | 2.91 | −2.50 | −22.98 | −3.51 | 19.6 |
| calibrationJigTranslationZ (mm) | −0.98 | −0.84 | −0.78 | −0.83 | −0.89 |

Table 4 shows the comparison between all Fluoro2Laser transformations calculated for the different calibration results.

The values represent the norm of the difference in translation between the compared Fluoro2Laser transformations, i.e., the calculation was performed thus:

$$\text{Fluoro2LaserComparison}_{12} = (\text{Fluoro2Laser}_1)^{-1} * \text{Fluoro2Laser}_2 \quad \text{Eq.2:}$$

$$\text{delta} = \text{norm}(\text{Fluoro2LaserComparison}(1{:}3,4)). \quad \text{Eq.3:}$$

The values of delta are shown in Table 4.

TABLE 4

Comparison of the Fluoro2Laser Transformations for All Calibrations.

| | Calibration #1 | Calibration #2 | Calibration #3 | Calibration #4 |
|---|---|---|---|---|
| Calibration #2 | 0.48 mm | | | |
| Calibration #3 | 0.58 mm | 0.11 mm | | |
| Calibration #4 | 0.47 mm | 0.08 mm | 0.12 mm | |
| Calibration #5 | 0.61 mm | 0.14 mm | 0.03 mm | 0.15 mm |

The mean value of the above comparisons is 0.28 mm, which is below the acceptance criteria threshold of 1 mm, therefore this test is passed.

Table 5 shows the projections of the same points in the Fluoroscope coordinate system into the same images, taken at various C-arm positions, using the different calibration results. The values shown in Table 5 represent the mean and max differences between the projections, translated from pixels into millimeters.

TABLE 5

Comparison of Fluoroscope to Image Projections for all Calibrations

| | Calibration #1 | Calibration #2 | Calibration #3 | Calibration #4 |
|---|---|---|---|---|
| Calibration #2 (mm) | mean 0.29 max 0.88 | | | |
| Calibration #3 (mm) | mean 0.34 max 1.01 | mean 0.09 max 0.47 | | |
| Calibration #4 (mm) | mean 0.23 max 0.69 | mean 0.11 max 0.36 | mean 0.13 max 0.43 | |
| Calibration #5 (mm) | mean 0.24 max 0.74 | mean 0.09 max 0.33 | mean 0.14 max 0.48 | mean 0.09 max 0.27 |

The mean value of the above comparisons is 0.18 mm, which is below the acceptance criteria threshold of 1 mm. Therefore, this test is passed.

Registration Algorithm Test Results.

Table 6 details the differences in Helix Jig position for the different registration images collected.

TABLE 6

Registration Data Collection

| Helix Jig position | Fluoro zoom [cm] |
|---|---|
| Table position [−59, −864, 930], Helix Jig positioned in COR | 42 |
| Table position [−59, −864, 740], Helix Jig not moved | 48 |
| Table position [−59, −864, 930], Helix Jig moved by ∼−10 cm in x-axis (relative to the COR) | 48 |
| Table position [−59, −864, 930], Helix Jig moved by ∼+20 cm in x-axis (relative to the COR) | 48 |
| Table position [−59, −864, 930], Helix Jig positioned in COR at an angle relative to the y-axis | 48 |

The difference between the Helix2Fluoro registration result for each registration image and the overall reference Helix2Fluoro for that Helix Jig position was calculated and is displayed in the Appendix graphs, showing translation matrix T elements [$T_X$, $T_Y$, $T_Z$] versus C-arm angle, for each Helix Jig position.

Table 7 shows the comparison of all Fluoro2Laser transformations calculated for the different registration images taken for the same Helix Jig position.

The values shown in Table 7 were calculated using Eq.2 and Eq.3 shown above and represent the mean and max differences between the Fluoro2Laser transformations calculated for the registration images taken for the same Helix Jig position, as well as the CDF95 values, i.e., the estimated upper threshold for 95%.

For each comparison between image registrations, delta was calculated for the direction perpendicular to both image angles only.

TABLE 7

Comparison of the Fluoro2Laser Transformations for all Registration Images at the same Helix Jig position

| Position | Mean delta [mm] | Max delta [mm] | CDF95 |
|---|---|---|---|
| 1 | 0.15 | 1.11 | 0.53 |
| 2 | 0.06 | 0.21 | 0.18 |
| 3 | 0.18 | 0.79 | 0.74 |
| 4 | 0.16 | 0.43 | 0.39 |
| 5 | 0.20 | 0.97 | 0.70 |

The mean value of the above comparisons is 0.15 mm, which is below the acceptance criteria threshold of 1 mm, therefore this test is passed.

Table 8 shows the comparison between all Fluoro2Laser transformations calculated for the different registration images taken with the C-arm at an AP position, and at an LAO90 position, across all Helix Jig positions.

The values shown in Table 8 were calculated using Eq.2 and Eq.3 shown above and represent the mean and max differences between the Fluoro2Laser transformations calculated for the registration images taken for the same C-arm position, as well as the CDF95 values, i.e., the estimated upper threshold for 95%.

For each comparison between image registrations, delta was calculated for the directions perpendicular to the image C-arm angle only (i.e., the z-axis delta was not taken into account for AP images comparison, and the x-axis delta was not taken into account for LAO90 images comparison).

TABLE 8

Comparison of the Fluoro2Laser transformations for registration images at the same C-arm angle

| C-arm angle | Mean delta [mm] | Max delta [mm] | CDF95 |
|---|---|---|---|
| AP | 0.40 | 1.07 | 1.06 |
| LAO90 | 0.09 | 0.23 | 0.18 |

The mean values of the above comparisons are 0.4 mm and 0.09 mm, which are below the acceptance criteria threshold of 1 mm. Therefore, this test is passed.

Table 9 shows the comparison between the reference Fluoro2Laser transformations calculated for the registration images for the different Helix Jig positions.

The values shown in Table 9 were calculated using Eq.2 and Eq.3 shown above.

TABLE 9

Comparison of the reference Fluoro2Laser transformations for the different Helix Jig positions

| | Position #1 | Position #2 | Position #3 | Position #4 |
|---|---|---|---|---|
| Position #2 | 0.88 mm | | | |
| Position #3 | 0.53 mm | 0.65 mm | | |
| Position #4 | 0.67 mm | 1.18 mm | 0.60 mm | |
| Position #5 | 0.38 mm | 0.76 mm | 0.18 mm | 0.50 mm |

The mean value of the above comparisons is 0.63 mm, which is below the acceptance criteria threshold of 1 mm. Therefore, this test is passed.

It will be appreciated by persons skilled in the art that the present invention is not limited to what has been particularly shown and described hereinabove. Rather, the scope of the present invention includes both combinations and sub-combinations of the various features described hereinabove, as well as variations and modifications thereof that are not in the prior art, which would occur to persons skilled in the art upon reading the foregoing description.

The invention claimed is:

1. A method for registering coordinate systems, comprising the steps of:
    positioning a calibration jig having markers that are opaque to an imaging modality in an imaged area, wherein the markers comprise at least two collinear marker quadruples having respective marker cross ratios;
    producing with the imaging modality an image of the markers;
    detecting the markers on the image;
    on the image identifying collinear image quadruples of the detected markers;
    computing respective image cross ratios of the collinear image quadruples;
    defining candidate lines by associating at least one collinear marker quadruple and at least one collinear image quadruple that have matching marker cross ratios and image cross ratios according to predefined criteria;
    performing respective registrations of the calibration jig with the image using pairs of the candidate lines;
    determining residuals of the registrations; and
    selecting one of the registrations wherein the pair of the candidate lines thereof is associated with a qualifying residual that is smaller than a predetermined value.

2. The method according to claim 1, wherein at least a portion of the candidate lines have a plurality of collinear image quadruples.

3. The method according to claim 1, further comprising the steps of:
    using the selected registration, reprojecting the markers onto the image; and
    thereafter establishing a new registration by locating others of the reprojected markers on the image.

4. The method according to claim 3, wherein locating others of the reprojected markers comprises determining a proximity between the reprojected markers and the detected markers.

5. The method according to claim 3 wherein locating others of the reprojected markers comprises scoring the reprojected markers according to a root mean square error of the reprojected markers and the detected markers.

6. The method according to claim 3, wherein establishing a new registration comprises minimizing a residual error of reprojecting the markers in six degrees of freedom.

7. The method according to claim 1, wherein the markers are identical in size.

8. A method for registering coordinate systems, comprising the steps of:
- positioning a calibration jig having radiopaque markers in an area irradiated by a fluoroscope, wherein the markers comprise at least two collinear marker quadruples having respective marker cross ratios;
- producing with the fluoroscope a fluoroscopic image of the markers;
- detecting the markers on the image;
- on the fluoroscopic image identifying collinear image quadruples of the detected markers;
- computing respective image cross ratios of the collinear image quadruples;
- defining candidate lines by associating at least one collinear marker quadruple and at least one collinear image quadruple that have matching marker cross ratios and image cross ratios according to predefined criteria;
- performing respective registrations of the calibration jig with the fluoroscopic image using pairs of the candidate lines;
- determining residuals of the registrations; and
- selecting one of the registrations wherein the pair of the candidate lines thereof is associated with a qualifying residual that is smaller than a predetermined value.

9. The method according to claim 8, wherein at least a portion of the candidate lines have a plurality of collinear image quadruples.

10. The method according to claim 8, further comprising the steps of:
- using the selected registration, reprojecting the markers onto the image; and
- thereafter establishing a new registration by locating others of the reprojected markers on the image.

11. The method according to claim 10, wherein locating others of the reprojected markers comprises determining a proximity between the reprojected markers and the detected markers.

12. The method according to claim 10 wherein locating others of the reprojected markers comprises scoring the reprojected markers according to a root mean square error of the reprojected markers and the detected markers.

13. The method according to claim 10, wherein establishing a new registration comprises minimizing a residual error of reprojecting the markers in six degrees of freedom.

14. The method according to claim 8, wherein the markers are identical in size.

15. An apparatus for registering coordinate systems, comprising:
- a calibration jig having radiopaque markers, wherein the markers comprise at least two collinear marker quadruples having respective marker cross ratios;
- a processor;
- a memory accessible to the processor storing programs and data objects therein, wherein execution of the programs cause the processor to perform the steps of:
- detecting the markers on a fluoroscopic image;
- on the image identifying collinear image quadruples of the detected markers;
- computing respective image cross ratios of the collinear image quadruples;
- defining candidate lines by associating at least one collinear marker quadruple and at least one collinear image quadruple that have matching marker cross ratios and image cross ratios according to predefined criteria;
- performing respective registrations of the calibration jig with the image using pairs of the candidate lines;
- determining residuals of the registrations; and
- selecting one of the registrations wherein the pair of the candidate lines thereof is associated with a qualifying residual that is smaller than a predetermined value.

16. The apparatus according to claim 15, wherein at least a portion of the candidate lines have a plurality of collinear image quadruples.

17. The apparatus according to claim 15, wherein the markers lie along a single axis.

18. The apparatus according to claim 15, wherein the processor is operative to perform the additional step of establishing a new registration on a reprojection of the markers onto the image using the selected registration by locating others of the reprojected markers on the image.

19. The apparatus according to claim 18, wherein locating others of the reprojected markers comprises determining a proximity between the reprojected markers and the detected markers.

20. The apparatus according to claim 15, wherein the markers are identical in size.

21. A method for registering coordinate systems, comprising the steps of:
- positioning a calibration jig having an axis of symmetry and markers that are opaque to an imaging modality in an imaged area, wherein the markers comprise a collinear marker quadruple having a marker cross ratio, the collinear marker quadruple being on the axis of symmetry;
- producing with the imaging modality an image of the markers;
- detecting the markers on the image;
- on the image identifying collinear image quadruples of the detected markers;
- computing respective image cross ratios of the collinear image quadruples;
- defining candidate lines by associating the collinear marker quadruple and at least one collinear image quadruple wherein the marker cross ratio and image cross ratios match according to predefined criteria;
- performing registrations of the calibration jig with the image using respective candidate lines;
- determining residuals of the registrations; and
- selecting one of the registrations wherein the candidate line thereof is associated with a qualifying residual that is smaller than a predetermined value.

22. An apparatus for registering coordinate systems, comprising:
- a calibration jig having radiopaque markers, wherein the markers comprise a collinear marker quadruple having a marker cross ratio;
- a processor;
- a memory accessible to the processor storing programs and data objects therein, wherein execution of the programs cause the processor to perform the steps of:
- detecting the markers on a fluoroscopic image;
- on the image identifying collinear image quadruples of the detected markers;
- computing respective image cross ratios of the collinear image quadruples;

defining candidate lines by associating the collinear marker quadruple and at least one collinear image quadruple wherein the marker cross ratio and image cross ratios match according to predefined criteria;

performing registrations of the calibration jig with the image using respective candidate lines;

determining residuals of the registrations; and selecting one of the registrations wherein the candidate line thereof is associated with a qualifying residual that is smaller than a predetermined value.

* * * * *